(12) United States Patent
Johnson

(10) Patent No.: US 9,907,607 B2
(45) Date of Patent: Mar. 6, 2018

(54) GUIDE AND FLEXIBLE SLEEVE FOR USE WITH CATHETERS

(75) Inventor: Theodore A. Johnson, St. Paul, MN (US)

(73) Assignee: ST. JUDE MEDICAL, ATRIAL FIBRILLATION DIVISION, INC., St. Paul, MN (US)

(*) Notice: Subject to any disclaimer, the term of this patent is extended or adjusted under 35 U.S.C. 154(b) by 1546 days.

(21) Appl. No.: 12/650,466

(22) Filed: Dec. 30, 2009

(65) Prior Publication Data
US 2011/0160720 A1    Jun. 30, 2011

(51) Int. Cl.
| | | |
|---|---|---|
| A61B 18/14 | (2006.01) | |
| A61B 5/042 | (2006.01) | |
| A61B 17/00 | (2006.01) | |
| A61B 17/22 | (2006.01) | |
| A61B 18/00 | (2006.01) | |
| A61B 90/00 | (2016.01) | |

(52) U.S. Cl.
CPC .......... *A61B 18/1492* (2013.01); *A61B 5/042* (2013.01); *A61B 2017/00084* (2013.01); *A61B 2017/00243* (2013.01); *A61B 2017/22038* (2013.01); *A61B 2018/00351* (2013.01); *A61B 2018/00577* (2013.01); *A61B 2018/00815* (2013.01); *A61B 2018/00821* (2013.01); *A61B 2018/1407* (2013.01); *A61B 2090/065* (2016.02); *A61B 2218/002* (2013.01)

(58) Field of Classification Search
CPC .............. A61B 5/042; A61B 2218/002; A61B 2017/00084; A61B 2017/00243; A61B 2017/22038; A61B 18/1492

USPC ........................................ 606/41, 42, 45, 49
See application file for complete search history.

(56) References Cited

U.S. PATENT DOCUMENTS

| | | | |
|---|---|---|---|
| 5,549,108 A | 8/1996 | Edwards et al. | |
| 6,926,714 B1* | 8/2005 | Sra ..................... | A61B 18/1492 606/41 |
| 6,964,660 B2 | 11/2005 | Maguire et al. | |
| 7,163,537 B2* | 1/2007 | Lee et al. ......... | 606/41 |
| 2005/0256521 A1* | 11/2005 | Kozel ............... | 606/41 |

FOREIGN PATENT DOCUMENTS

WO    WO-2008/084239    7/2008

* cited by examiner

*Primary Examiner* — Michael Peffley
*Assistant Examiner* — Samantha Good
(74) *Attorney, Agent, or Firm* — Dykema Gossett PLLC

(57) ABSTRACT

Embodiments of a guide and flexible sleeve for use with catheters for ablation or other medical procedures are disclosed. An exemplary catheter comprises a guide element having a proximal end and a distal end, the distal end configurable in a desired shape. A flexible sleeve is conformable to the guide element so that the flexible sleeve slides over the guide element, the flexible sleeve has a proximal end and a distal end. A controller couples to the flexible sleeve. The controller operates to move the flexible sleeve at least part way between the distal end of the guide element and the proximal end of the guide element. At least one ablation element disposed at the distal end of the flexible sleeve operates to form a substantially continuous ablative lesion when the flexible sleeve is in contact with a contiguous volume of target tissue.

18 Claims, 12 Drawing Sheets

GUIDE AND FLEXIBLE SLEEVE FOR USE WITH CATHETERS

BACKGROUND OF THE INVENTION a. Field of the Invention

This invention relates generally to medical instruments, and, more specifically, to a guide and flexible sleeve for use with catheters for ablation or other medical procedures.

b. Background Art

Catheters are flexible, tubular devices that are widely used by physicians performing medical procedures to gain access into interior regions of the body. Careful and precise positioning of the catheters within the body is important to successfully completing such medical procedures. It is well known that benefits can be and/or are gained by using catheters to form lesions in tissue if the depth and location of the lesions being formed can be controlled. For example, it can be desirable to elevate tissue temperature to around 50° C. until lesions are formed via coagulation necrosis, which changes the electrical properties of the tissue. Lesions can be and/or are formed at specific locations in cardiac tissue via coagulation necrosis to lessen or eliminate undesirable atrial fibrillation.

Several difficulties can be and/or are encountered, however, when attempting to form lesions at specific locations using some existing ablation electrodes. One such difficulty encountered with existing ablation catheters is how to locate the tissue and maintain catheter contact with the tissue at the desired location during the procedure. These assessments are not readily determined using conventional fluoroscopy techniques. Instead, the physician locates and maintains contact between the catheter and the tissue based on his/her experience using the catheter. Such experience only comes with time, and can be and/or are quickly lost if the physician does not use the catheter on a regular basis. In addition, when forming lesions in a heart, the beating of the heart further complicates matters, making it difficult to maintain sufficient contact pressure in a fixed location between the catheter and the tissue for a sufficient length of time to form a desired lesion. If the contact between the catheter and the tissue cannot be properly maintained, a quality lesion is unlikely to be created.

BRIEF SUMMARY OF THE INVENTION

It is desirable to be able to maintain contact and create desired lesions in tissue, including in a moving surface (e.g., the heart wall). In various embodiments, a guide and flexible sleeve for use with catheters for ablation or other medical procedures are disclosed. The guide can be and/or is preformed (i.e., prior to the procedure) to a desired shape (e.g., a circular shape). Once positioned adjacent a tissue to be ablated, one or more ablation element can be and/or are activated and the flexible sleeve can be and/or is retracted from a distal end of the guide to form a lesion substantially conforming to the shape of the guide that is in contact with the tissue. The catheters disclosed herein can be and/or are used to make spot or linear lesions along the length of the guide according to the shape of the guide.

In an exemplary embodiment, a catheter can comprise a guide element having a proximal end and a distal end, the distal end configurable in a desired shape. A flexible sleeve is conformable to the guide element so that the flexible sleeve slides over the guide element, the flexible sleeve has a proximal end and distal end. A controller is attached to the flexible sleeve. The controller is operable to move the flexible sleeve at least part way between the distal end of the guide element and the proximal end of the guide element. At least one ablation element is provided at the distal end of the flexible sleeve. The at least one ablation element is operable to form an ablative lesion when the flexible sleeve is in contact with a target tissue.

In another exemplary embodiment, a catheter comprises a unitary flexible tubing having a proximal end and a distal end defining substantially an entire length of the catheter. A guide element is provided having a proximal end and a distal end, the distal end preformed in a desired shape. A flexible sleeve is conformable to the guide element so that the flexible sleeve slides over the guide element, the flexible sleeve having a proximal end and a distal end, the combination guide element and flexible sleeve insertable through the unitary flexible tubing. A controller is attached to the flexible sleeve and extending through the unitary flexible tubing for operation outside of a patient's body, the controller operable to affect travel of the flexible sleeve over the guide element in two directions. At least one ablation element is provided at the distal end of the flexible sleeve, the at least one ablation element operable to form an ablative lesion when the flexible sleeve is in contact with a target tissue.

In yet another exemplary embodiment, a catheter comprises a flexible tubing defining substantially an entire length of the catheter. Guide means is provided having a proximal end and a distal end, the distal end preformed in a desired shape. A flexible sleeve is conformable to the guide means so that the flexible sleeve slides over the guide means, the flexible sleeve having a proximal end and a distal end, the guide means and flexible sleeve insertable through the flexible tubing for positioning adjacent a tissue. Control means is attached to the flexible sleeve and extending through the flexible tubing for operation outside of a patient's body to move the flexible sleeve back and forth over the guide means. Ablation means is provided at the distal end of the flexible sleeve, the ablation means operable to form an ablative lesion when the flexible sleeve is in contact with a target tissue.

In still further embodiments, the guide element is a guide wire and/or a mapping catheter. The guide element can be and/or are preformed in the desired shape. The desired shape of the guide cancan be and/or are, e.g., circular. A collar can be and/or are provided on the distal end of the guide element, the collar stopping travel of the flexible sleeve when the flexible sleeve comes into contact with the collar. The guide element can include an irrigation conduit with at least one irrigation port.

In still further embodiments, the flexible sleeve is positioned at the distal end of the guide element initially during an ablation procedure, and the guide element is retracted toward the proximal end of the guide element during the ablation procedure, wherein retrograde motion creates a lesion on the tissue substantially conforming to the desired shape of the guide element. The flexible sleeve can include an insulated portion and an active portion. The insulated portion is provided over a conducting portion. The conducting portion is electrically connected to the active portion, the conducting portion delivering electrical energy to the active portion, and the active portion is the ablation element.

In other embodiments, the ablative element includes at least one electrode mounted to an outer surface of the flexible portion. At least one sensor can be and/or are mounted to an outer surface of the flexible portion. For example, the sensor can be and/or are a thermistor, thermocouple, a mapping sensor, or a contact sensor.

Still other features of a guide for catheters are disclosed.

DETAILED DESCRIPTION OF THE INVENTION

Exemplary embodiments of a guide and flexible sleeve for use with catheters for ablation or other medical procedures, along with methods for creating ablative lesions, are depicted in the figures. Exemplary systems comprise a catheter which can be and/or are inserted into the patient, e.g., an ablation catheter for forming ablative lesions inside the patient's heart. During an exemplary ablation procedure, a user (e.g., the patient's physician or a technician) can insert the catheter into one of the patient's blood vessels, e.g., through the leg or the patient's neck. The user, guided by a real-time fluoroscopy imaging device, moves the catheter into the patient's heart.

When the catheter reaches the patient's heart, sensors at the distal portion of the catheter can be and/or are implemented to electrically map the myocardium (i.e., muscular tissue in the heart wall) and locate a target tissue. After locating the target tissue, the user moves the catheter into contact with the target tissue before applying ablative energy to form an ablative lesion or lesions. Implementing the guide having a preformed shape and sliding the flexible sleeve over the guide during the ablation procedure, the user is able to provide the appropriate level of contact at the target area in order to form quality ablative lesions without damaging surrounding tissue in the heart or other tissues or anatomical structures elsewhere in the patient's body.

Accordingly, embodiments of the present invention provide a number of advantages, including, for example, the ability to apply a reasonable amount of ablative energy to a target tissue while mitigating tissue contact problems. The invention also facilitates enhanced tissue contact in difficult environments (e.g., during lesion formation on a moving surface inside a beating heart, and adjacent other sensitive tissues or anatomical structures).

Figure 1:
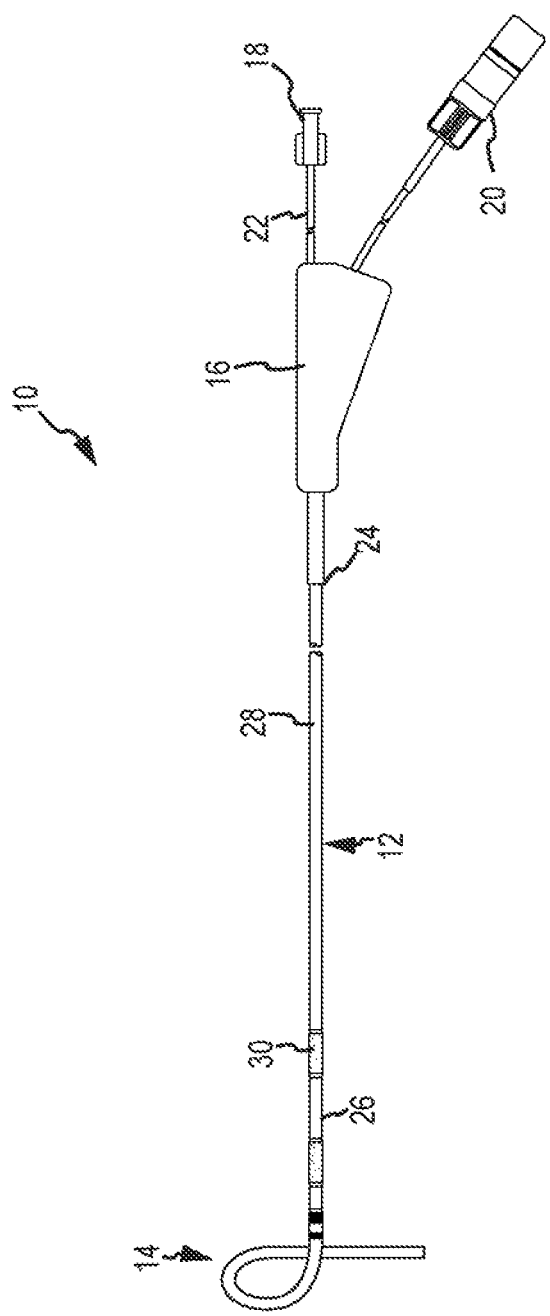
FIG. 1 illustrates a first exemplary catheter.

FIG. 1 illustrates one type of an exemplary single-use catheter 10 generally including a flexible tubing 12, a tip assembly 14, a Y connector 16, a luer device 18, and an electrical connector 20. The electrical connector 20 establishes electrical connection with a power source (not shown) that operates ablative element(s) and/or sensors at the tip assembly 14 to perform, for example, ablation procedures, mapping or pacing procedures, or to perform other aspects of a medical procedure.

Although it will become evident that aspects of the exemplary catheter 10 are applicable to a variety of medical procedures and end uses, the invention will be described principally in the context of a specific example of an ablation catheter. Specifically, the catheter 10 as shown in FIG. 1 is believed to be particularly advantageous as an ablation catheter for creating endocardial lesions during cardiac ablation procedures to treat arrhythmias, and also for cardiac electrophysiological mapping and delivering diagnostic pacing stimuli. However, the invention and the appended claims are not intended to be limited to any specific type of catheter (e.g., steering catheters can also be used), including but not limited to specific examples or embodiments described herein, except when explicitly defined as such in the appended claims.

The Y-connector 16 separates a fluid tube 22 from electrical lead wires extending between the tip assembly 14 and the electrical connector 20. That is, the fluid tube 22 and the lead wires forward of the Y-connector 16 pass internally through The tubing 12, while aft of the Y-connector 16, the fluid tube 22 and the wire leads are exposed and separated for connection to a fluid source (not shown) and a power source, respectively. The electrical connector 20 can be and/or is a known connector that can be and/or is engaged to a power source or power supply with, for example, plug-in connection. One suitable electrical connector is a 14 pin REDEL® plastic connector commercially available from LEMO of Rohnert Park, Calif., although other connectors from various manufacturers can likewise be utilized.

The luer device 18 in the depicted embodiment, as known in the art, can be and/or is used to open or close a flow path so that fluid can be and/or is passed through the Y-connector 16 and the tubing 12 to the tip assembly 14 for irrigation purposes. The luer device 18 can be and/or is considered optional for certain procedures.

The flexible tubing 12 includes a proximal end 24 coupled to the Y-connector 16, a distal end 26 coupled to the tip assembly 14, and an axial length extending between the proximal and distal ends 24 and 26. In general, the flexible tubing 12 can be and/or is fabricated according to known processes, such as extrusion processes. The tubing 12 can be and/or is fabricated from any suitable tubing material known in the art of medical instruments, such as engineered nylon resins and plastics, including but not limited to PEBAX® tubing of Ato Fina Chemicals, France.

In an exemplary embodiment, the tubing 12 includes a first portion 28 of the tubing 12 between the Y connector and the tip assembly 14, and a second portion 30 of the tubing 12 including the distal or end portion of the tubing 12 extending to the tip assembly 14. In an exemplary embodiment, the first portion 28 and the second portion can be and/or are fabricated from different materials, grades of materials, and/or thicknesses of materials for enhanced performance and flexibility of the tubing 12 in use of the catheter assembly 10, as will be explained in more detail below. It is noted, however, that although the tubing 12 can have different portions or "zones", the tubing 12 is manufactured as a unitary piece.

For example, in one embodiment, the first portion 28 of the tubing 12 can include, for example a braided material that is comparatively rigid and kink resistant. The first portion 28 can be and/or is formed with different portions of braided material, semi-soft material, and soft material fused to one another so that the first portion 28 becomes increasingly flexible along the axial length as the tube portion 28 approaches the second portion 30. The second portion 30 of the tubing 12 can include a soft and flexible material. In the illustrated embodiment, each of the tubing portions 28 and 30 share a common outside diameter of, for example, 7 French, although in other embodiments, the tubing portions 28 and 30 can be and/or are another size.

Additionally, and as shown in FIG. 1, the first portion 28 extends for the vast majority of the axial length of the tubing 12 between the proximal end 24 and distal end 26. The second portion 30 of the tubing 12 extends for a much shorter length than the first portion 28. By way of example only, in a specific embodiment the first portion 28 extends for an axial length of about 126.3 cm, the second portion 30 extends for an axial length of about 0.8 cm to 2.2 cm, although other relative lengths of the tube portions can likewise be employed in other embodiments. The different relative lengths of the tube portions 28 and 30, as well as the different flexible properties of the tube portions 28 and 30, allows the tip assembly 14 to be more precisely positioned within a patient's body, while also avoiding problems of kinks and excessive deflection of the tubing 12 along the majority of its length during use and handling.

Also in exemplary embodiments, the catheter 10 can be constructed to have different flexibilities along the length of tubing 12, particularly in the distal region. Typically, the distal end 26 (where the tip assembly 14 is located) is desired to be the most flexible. The proximal end 28 is desired to have less flexibility. Still additional portions can be and/or are provided, with the proximal portions having less and less flexibility.

The flexibility can be determined by material properties and/or thickness. Thus, the tubing 12 can be made to have varying material properties along its length toward the distal end, so that the different portions will have different flexibilities. The shaft can also decrease in thickness toward the distal end 26. A thinner wall of the tubing 12 results in greater flexibility, while a thicker wall of the tubing 12 results in less flexibility. Flexibility can change either continuously/gradually or in abrupt steps.

The unitary construction of the flexible tubing of the catheter 10 is believed to provide manufacturing benefits, and also performance benefits, in relation to conventional, and more complicated, catheter constructions for use with stereotactic systems. The catheter 10 can be manufactured without joints, ensuring high reliability and safety of the catheter 10. The unitary tubing is easier to manufacture, and takes less time to manufacture. Eliminating junctions in the shaft also reduces or altogether eliminates undesirable stiffness. The unitary flexible tubing can extend along substantially the entire length of the catheter body, and can have a distal end to be coupled to the tip assembly 14 and a proximal end to be coupled to a handle (not shown). Alternatively, the unitary flexible tubing can extend along a portion of the catheter body, but can be and/or is attached to additional components to form the entire length of the catheter body. For example, the unitary flexible tubing with no fused connections can be and/or is fused with another flexible tubing to form the entire length of the catheter body.

In operation, the distal end of the catheter 10 including the tip assembly 14 is navigated to the site in the body where a medical procedure, such as an atrial mapping, pacing and ablation are to occur. The distal end can extend, for example, into a heart chamber of a patient. Once the distal end is in the chamber, imaging techniques can be and/or are utilized to precisely position the tip assembly 14 for performance of the procedure at a specific location, as will be described in more detail below.

It is noted that other components typical of systems which are conventionally implemented for tissue ablation or for other therapeutic procedures implemented via catheters (e.g., delivery of a drug or therapeutic agent) are not shown or described herein for purposes of brevity. Such components can nevertheless also be provided as part of, or for use with, the catheter 10. For example, these systems commonly include or are used in conjunction with an ECG recording system, and/or various controls for performing the ablation procedure. Such components are well understood in the medical devices arts and therefore further explanation is not necessary for a complete understanding of the invention.

Figure 2:
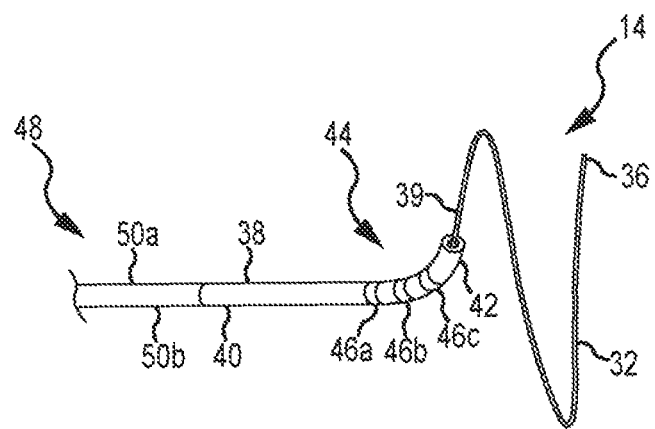
FIG. 2 is a magnified view of a distal end portion of the catheter shown in FIG. 1.

FIG. 2 is a magnified view of a tip assembly 14 of the catheter 10 shown in FIG. 1. The tip assembly 14 can be and/or is coupled to the tube portion 12 at one end and provide through a sheath (not shown) for insertion through the patient's body.

The tip assembly 14 can include a guide element 32 having a proximal end 34 and a distal end 36. The length of the guide element 32 extending between the proximal end 34 and the distal end 36 of the tip assembly 14 can be and/or is configurable in a desired shape. For example, guide element 32 can be and/or is a guide wire which is formed in a helical, circular shape, as shown in FIG. 2. Of course any suitable shape can be and/or is employed (e.g., semi-circular, oval, rectangular, triangular, etc.).

The tip assembly 14 can also include a flexible sleeve 38 having a proximal end 40 and a distal end 42. The flexible sleeve 38 is made of a material which enables the flexible sleeve 38 to conform to the shape of the guide element 32 so that the flexible sleeve 38 can be slid over the guide element 32. In an exemplary embodiment, the flexible sleeve 38 is made of a biologically compatible plastic or polymer material. Alternatively, the flexible sleeve 38 can be and/or is made of any material and provided with a suitable coating (e.g., Teflon® coating).

The tip assembly 14 is particularly suited for ablation procedures wherein radio frequency waves are delivered at the site of an abnormal pathway in the body. Radiofrequency (RF) energy can therefore be coupled to biological tissue surrounding the catheter tip. Ablation procedures are typically used, for example, within the interior chambers of the heart to thermally ablate cardiac tissue.

In this regard, the flexible sleeve 38 can include at least one ablation element 44 near the distal end 42 of the flexible sleeve 38. The ablation element 44 can be and/or is energized for an ablation procedure, as is well known in the medical devices arts, for example, using RF energy. Accordingly, the ablation element 44 is operable to form an ablative lesion when the ablation element 44 on the flexible sleeve 38 are in contact with a target tissue.

In an exemplary embodiment, the ablation element 44 includes one or more electrodes. In FIG. 2, three ring electrodes 46a-c are shown. However, any suitable number and/or type of electrodes can be and/or are provided, and will depend at least to some extent on design considerations and the intended end-use. The electrodes 46*a-c* are spaced from one another by dielectric materials as is known in the art. In one example, the electrodes 46*a-c* can be and/or are 8 Fr electrodes that are, for example, 2 mm in height. The electrodes 46*a-c* can be and/or are fabricated from 90% platinum and 10% iridium, or other materials known in the art. The electrodes 46*a-c* can be and/or are visually recognizable under fluoroscopic exposure. While each electrode 46*a-c* is formed as an integral unit, the individual electrodes 46*a-c* can include multiple electrode elements. The electrodes 46*a-c* can additionally be operated to record intracardiac signals and to provide pacing signals.

A controller 48 can be and/or is operatively associated with the tip assembly. In an exemplary embodiment, the controller 48 can include one or more pull wires 50*a-b* attached to the flexible sleeve 38 and extending through the tubing 12 of the catheter 10 (shown in FIG. 1) and out the electrical connector 20 near the handle 16 of the catheter 10, so that the pull wires 50*a-b* are operable by the user. The pull wires 50*a-b* can further be connected to a lever arm or rotational device (not shown) that is provided on or near the catheter handle to facilitate positioning and operation by the user. Regardless of the specific implementation, operation of the pull wires 50*a-b* by the user enables the flexible sleeve 38 to travel in two directions, as illustrated by the arrows shown in FIGS. 3*a* and 3*d*. This travel moves the flexible sleeve 38 at least part way between the distal end 36 of the guide element 32 and the proximal end 34 of the guide element 32. Exemplary movement of the flexible sleeve 38 for an ablation procedure can be and/or is better understood with reference to FIGS. 3*a-d*.

Figure 3A:
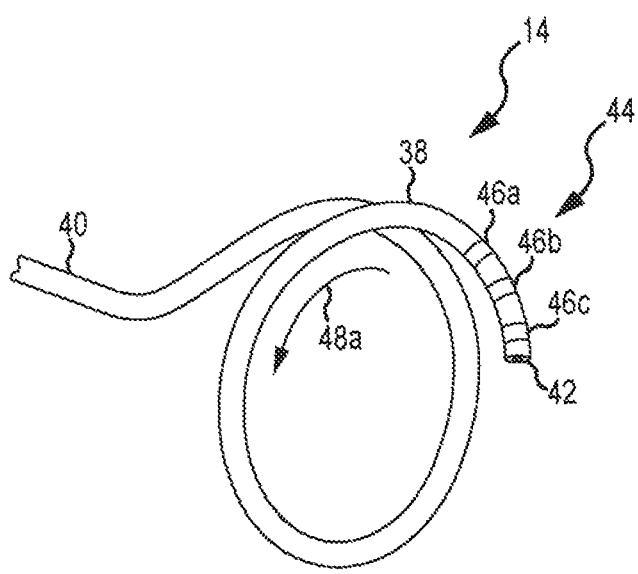
FIGS. 3a-d show the tip assembly 14 as it can be and/or are moved over the guide element.
Figure 3B:
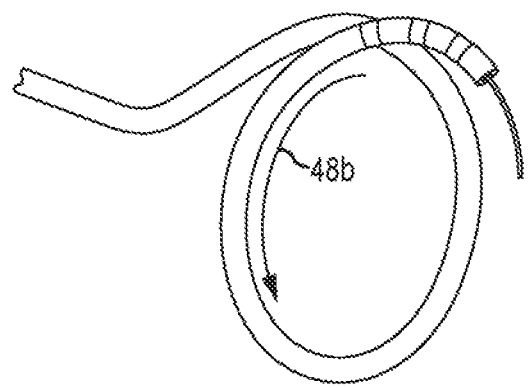
Figure 3C:
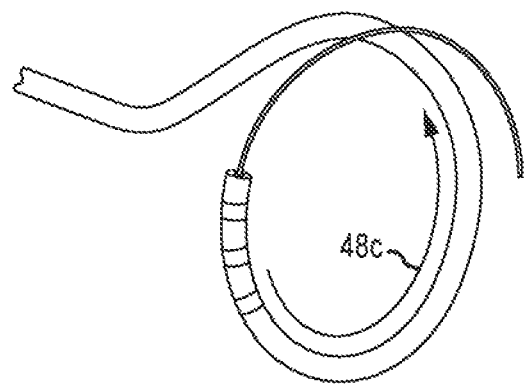
Figure 3D:
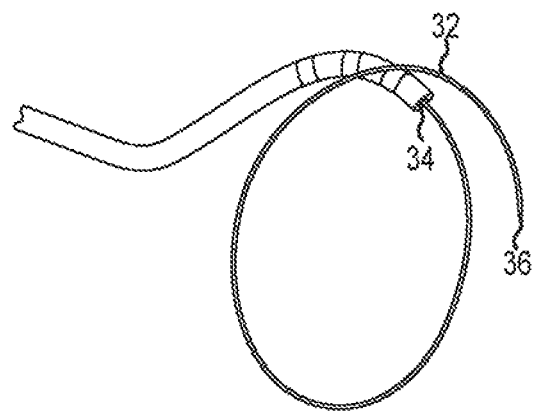

FIGS. 3*a-d* show the tip assembly 14 as it can be and/or is moved over the guide element 32. In FIG. 3*a*, the flexible sleeve 38 is shown as it can be and/or is moved into a fully extended position. In the fully extended position, the distal end 42 of the flexible sleeve 38 is at the distal end 36 of the guide element 32 (see FIG. 2). During and exemplary procedure, the flexible sleeve 38 is moved to the fully extended position prior to contacting the tissue and beginning the procedure. Once positioned against the tissue in the desired location, the ablative element 44 can be and/or is activated, e.g., by delivering RF energy to the ring electrodes 46*a-c*. Once a sufficient lesion has been formed in the fully extended position, the user can gradually retract the flexible sleeve 38, e.g., by operating the controller 38 to withdraw the flexible sleeve 38 generally in the direction of arrow 48*a* in FIG. 3*a* so that the flexible sleeve 38 is in a partially retracted position as illustrated in FIG. 3*b*. The user can continue to retract the flexible sleeve 38 (again, by operating the controller 38) to withdraw the flexible sleeve 38 generally in the direction of arrow 48*b* in FIGS. 3*b* and 38*c* in FIG. 3*c* so that the flexible sleeve 38 continues to retract as illustrated in FIG. 3*c*, until the flexible sleeve 38 is in a fully retracted position, as illustrated in FIG. 3*d*.

It is noted the operation illustrated in FIG. 3*a-d* is not intended to illustrate discrete positions of the flexible sleeve 38, but rather to illustrate general movement from a fully extended position (as shown in FIG. 3*a*) wherein the distal end 42 of the flexible sleeve 38 is at the distal end 36 of the guide element 32; to a fully retracted position (as shown in FIG. 3*d*) wherein the distal end 42 of the flexible sleeve 38 is at the proximal end 34 of the guide element 32. It is also noted that this motion can be and/or is a "fluid" or "smooth" motion (e.g., where the user moves the flexible sleeve 38 at a constant velocity); or the motion can be and/or is more segmented (e.g., where the user moves the flexible sleeve 38 to various positions and maintains the flexible sleeve 38 at one or more of these positions for a period of time). Specific operation will depend on the desired end-result, among other considerations for lesion formation.

Figure 4:
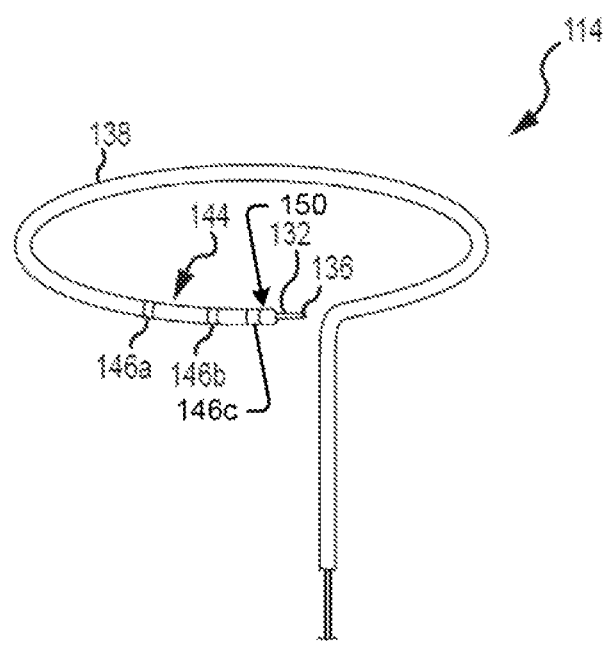
FIG. 4 shows another embodiment of the tip assembly.

FIG. 4 shows another embodiment of the tip assembly 114. It is noted that 100-series reference numbers are used to refer to like components already described above, and therefore cannot be described again here with reference to FIG. 4.

In this embodiment, the tip assembly 114 also includes a flexible sleeve 138 having an ablation element 144 with ring electrodes 146*a-c*. The flexible sleeve 138 conforms to a guide element 132. However, in this embodiment, the guide element 132 includes a collar 150 at the distal end 136. The collar 150 can have any suitable configuration, such as an end cap, rounded tip, etc. The collar 150 is provided to stop travel of the flexible sleeve 138 when the flexible sleeve 138 comes into contact with the collar 150. Accordingly, the flexible sleeve 138 does not overrun the guide element 132. In addition, the user receives tactile feedback so that the user can know when the flexible sleeve 138 is properly positioned in the fully extended position (e.g., as shown in FIG. 3*a*).

Figure 5:
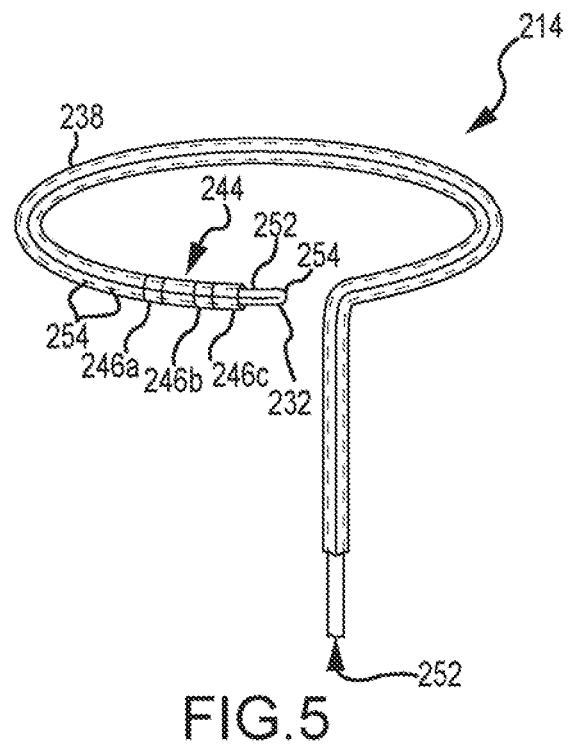
FIG. 5 shows another embodiment of the tip assembly.

FIG. 5 shows another embodiment of the tip assembly 214. It is noted that 200-series reference numbers are used to refer to like components already described above, and therefore cannot be described again here with reference to FIG. 5.

The tip assembly 214 includes a flexible sleeve 238 having an ablation element 244 with ring electrodes 246*a-c*. The flexible sleeve 238 conforms to a guide element 232. In this embodiment, the guide element 232 includes a guide wire 252 provided with a coating 254. The guide wire 252 can be and/or is a metal, plastic or polymer which can be and/or is either preformed during manufacture or by the user (e.g., prior to introducing the guide wire into the catheter sheath). The coating 254 can be and/or is any coating suitable for use in a biological system (e.g., Teflon® coating). In addition to blunting the distal end 236, the coating 254 serves as a barrier and keeps the guide wire 252 from being exposed to the tissue.

Figure 6:
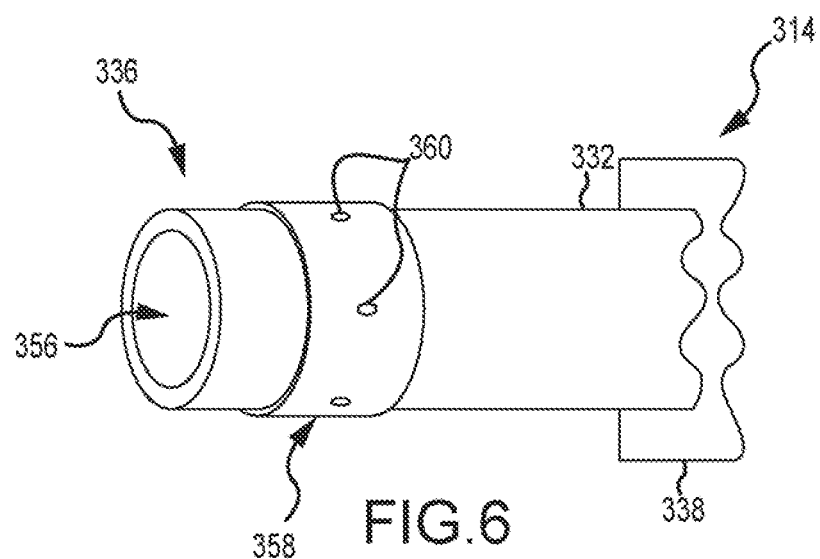
FIG. 6 shows a close up view of another tip assembly 314 which might be implemented with an irrigated catheter.

FIG. 6 shows a close up view of another tip assembly 314 which might be implemented with an irrigated catheter. In FIG. 6, only the distal end 336 of the guide element 332 is shown. It is noted that 300-series reference numbers are used to refer to like components already described above, and therefore cannot be described again here with reference to FIG. 6.

The tip assembly 314 includes a flexible sleeve 338. The flexible sleeve 338 conforms to a guide element 332. In this embodiment, the guide element 332 includes a lumen 356 formed along the length of the central axis of the guide element 332. The guide element 332 can be and/or is, for example, a braided polyimide tube that maintains the flow path through the lumen 356 in all orientations of the tip assembly 314, without compromising the flexibility of the tubing. The distal end 336 of the guide element 332 is fitted with an irrigated collar 358 including one or more irrigation ports 360. The lumen 356 is in fluid communication with the luer 18 (FIG. 1) on one end and with the irrigation ports 360 of the tip assembly 314 at the other. The distal end 336 of the guide element 332 can be and/or is closed. Or the distal end 336 of the guide element 332 can be and/or is open, thereby forming another fluid port. In any event, an irrigation fluid, such as saline, can be and/or is injected through the tip assembly 314. Fluid can be and/or is enabled to flow through the catheter 10 and be released at the tissue, e.g., to enhance contact and promote ablative coupling with the tissue, as a cooling fluid, as an ablative fluid, or for any other reason where an irrigated catheter can be and/or is used.

In addition, the irrigated collar 358 further serves a similar function to that of the collar 50 shown in FIG. 4, to prevent the flexible sleeve 338 from passing over the irrigated collar 358. By stopping the flexible sleeve 338 behind the irrigated collar 358, the flexible sleeve 338 does not block or otherwise interfere with delivery of the fluid at the fluid ports.

It is noted that the tip assembly 314 shown in FIG. 6 is provided only as one example of how the tip assembly might be implemented with an irrigated catheter. Of course other embodiments are also contemplated, for example, having multiple fluid ports along the length of the guide element, different fluid ports at different locations and/or for different types of fluids, and so forth. It is also noted that the tip assembly can be and/or is used with any types of fluid, including but not limited to, cooling fluids and/or therapeutic fluids.

Figure 7:
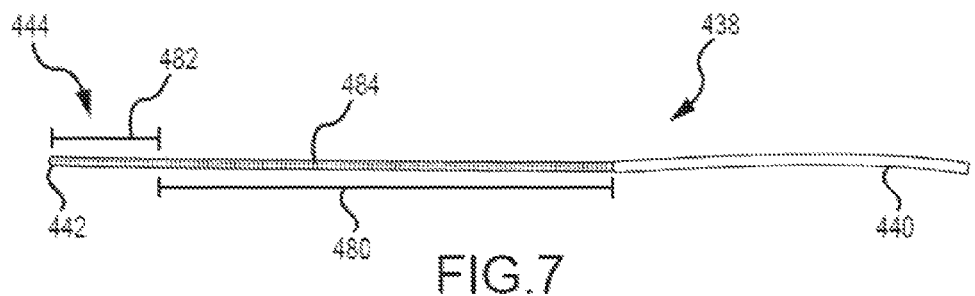
FIG. 7 shows another flexible sleeve which can be and/or are implemented with a tip assembly.
Figure 8:
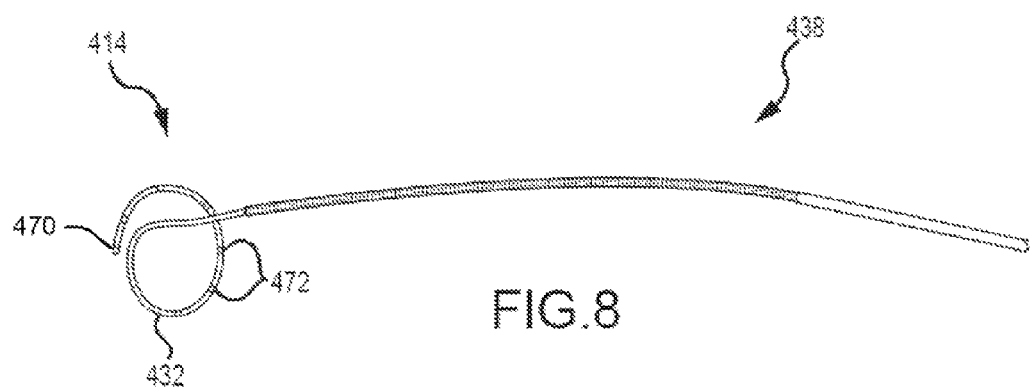
FIG. 8 shows a tip assembly having a guide element and the flexible sleeve from FIG. 7.

FIG. 7 shows another flexible sleeve 438 which can be and/or is implemented with a tip assembly. FIG. 8 shows the tip assembly 414 of the catheter 10 shown in FIG. 1, wherein the tip assembly 414 includes the flexible sleeve from FIG. 7 and a guide element 432. The tip assembly 414 can be and/or is coupled to the tube portion 12 of the catheter 10 in FIG. 1 at one end, and provided through a sheath (not shown) for insertion into the patient's body.

The tip assembly 414 can include a flexible sleeve 438 having a proximal end 440 and a distal end 442. The flexible sleeve 438 is made of a material which enables the flexible sleeve 438 to conform to the shape of the guide element 432 so that the flexible sleeve 438 can be slid over the guide element 432. In an exemplary embodiment, the flexible sleeve 438 is made of a biologically compatible plastic or polymer material. Alternatively, the flexible sleeve 438 can be and/or is made of any material and provided with a suitable coating (e.g., Teflon® coating).

The guide element 432 (FIG. 8) has a proximal end and a distal end. The length of the guide element 432 extending between the proximal end and the distal end of the tip assembly 414 can be and/or is configurable in a desired shape. In this embodiment, the guide element 432 can be and/or is a mapping catheter 470 which is formed in a helical, circular shape, or in any other suitable shape. The mapping catheter 470 can include one or more sensor electrodes 472. During use, the mapping catheter 470 can be and/or is inserted adjacent the tissue so that the tissue can be mapped. Following the mapping operation, the flexible sleeve 438 can be and/or is advanced to the distal end of the mapping catheter 470 and operated for the ablation procedure.

In this regard, the flexible sleeve 438 can include an insulated portion 480 and an active portion 482. The active portion 482 can extend for a length of about 2 mm up to about 8-10 mm, although other lengths can also be utilized depending on design/use considerations. The insulated portion 480 is provided over a conducting portion 484. The conducting portion 484 is electrically connected to the active portion 482 on one end, and to wiring or other electrical conductors provided through the lumen of the catheter 10 (FIG. 1) so that the conducting portion 484 delivers electrical energy to the active portion 482 of the flexible sleeve 438. Accordingly, in this embodiment the active portion 482 is the ablation element 444. The ablation element 444 can be and/or is energized for an ablation procedure, as is well known in the medical devices arts, for example, using RF energy. Accordingly, the ablation element 444 is operable to form an ablative lesion when the ablation element 444 (i.e., the active portion 482 on the flexible sleeve 438 is in contact with a target tissue.

It is noted that the active portion 482 can have any suitable configuration, including one or more active areas along the length of the flexible sleeve 438. In addition, any suitable number and/or type of electrodes and/or other sensors can also be provided, and will depend at least to some extent on design considerations and the intended end-use.

As already discussed above, a controller can be and/or is operatively associated with the tip assembly 414. The controller can be and/or is operated similarly to that already described above (e.g., including one or more pull wires), and therefore is not shown and described again with reference to the tip assembly 441.

Figure 9A:
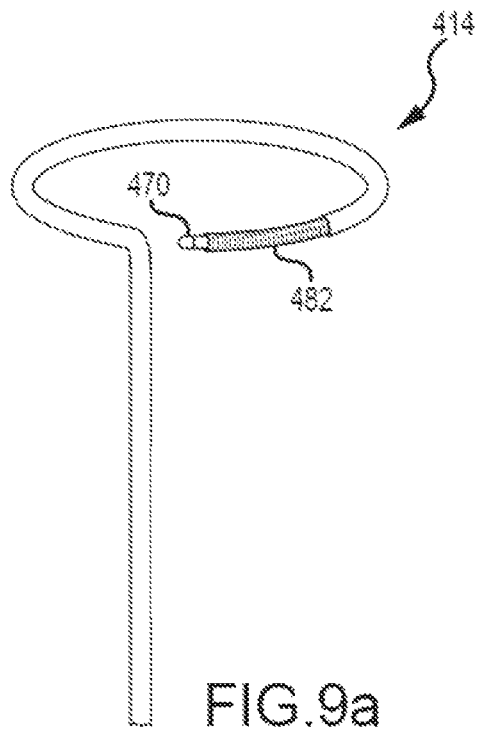
FIGS. 9a-b shows the flexible sleeve in (a) a fully extended position relative to the guide element; and (b) in a fully retracted position relative to the guide element.
Figure 9B:
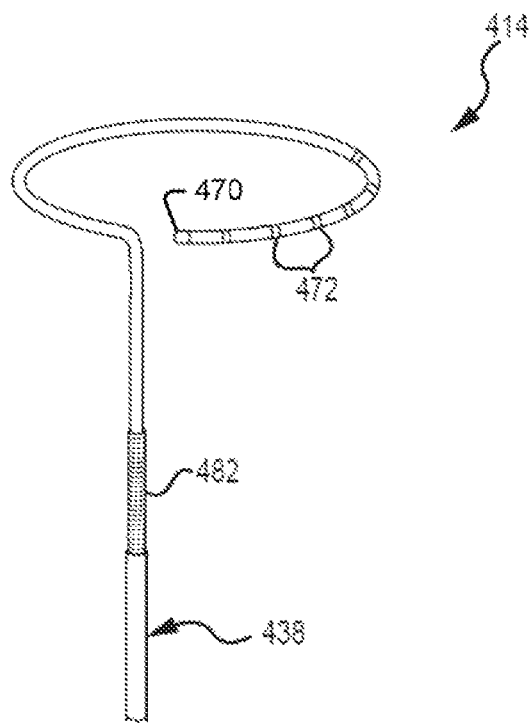

FIGS. 9a-b shows the flexible sleeve 438 in (a) a fully extended position relative to the guide element 431; and (b) in a fully retracted position relative to the guide element 431. FIGS. 10a-e illustrates how the flexible sleeve 438 can be and/or is moved over the guide element 432 between the extended position and the retracted position. As mentioned above, the tip assembly 414 can have any suitable shape and/or configuration. For purposes of illustration, in FIGS. 10a-e, the tip assembly 414 is shown having a more flattened configuration.

Figure 10A:
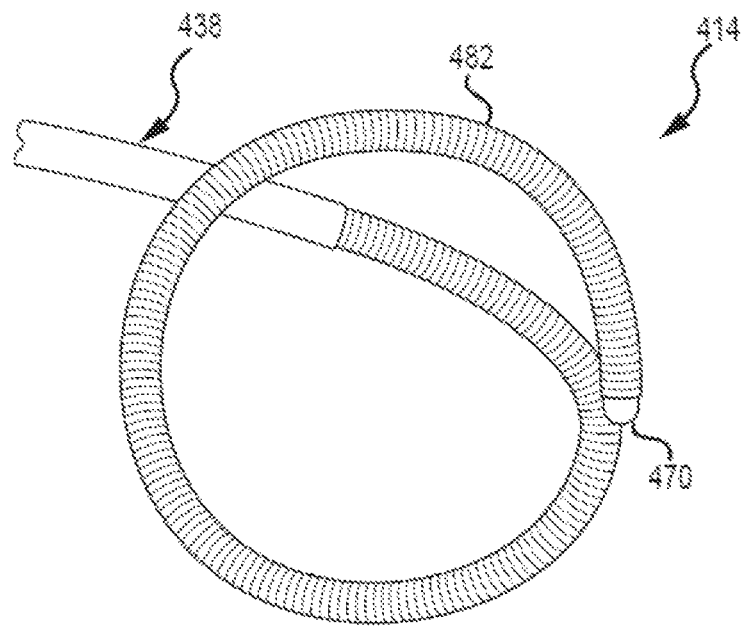
FIGS. 10a-e shows the tip assembly from FIG. 8 and illustrates how the flexible sleeve can be and/or are moved over the guide element.
Figure 10B:
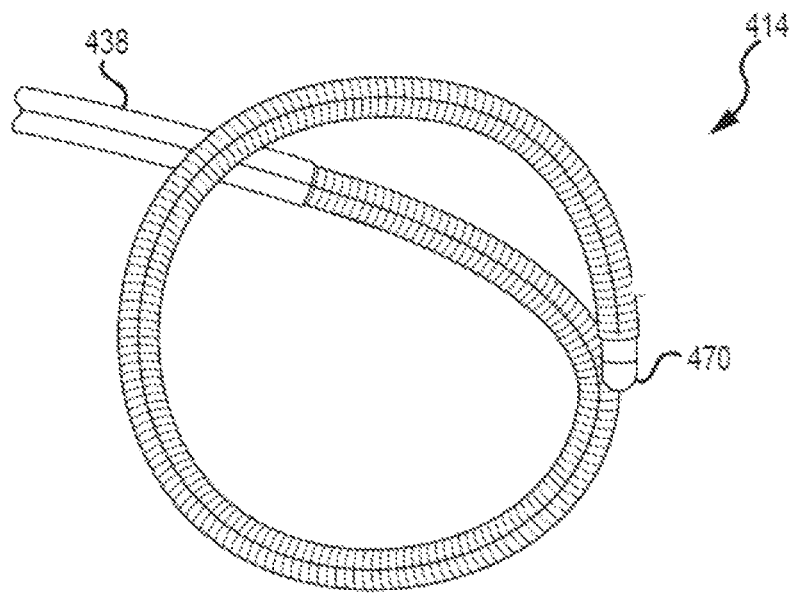
Figure 10C:
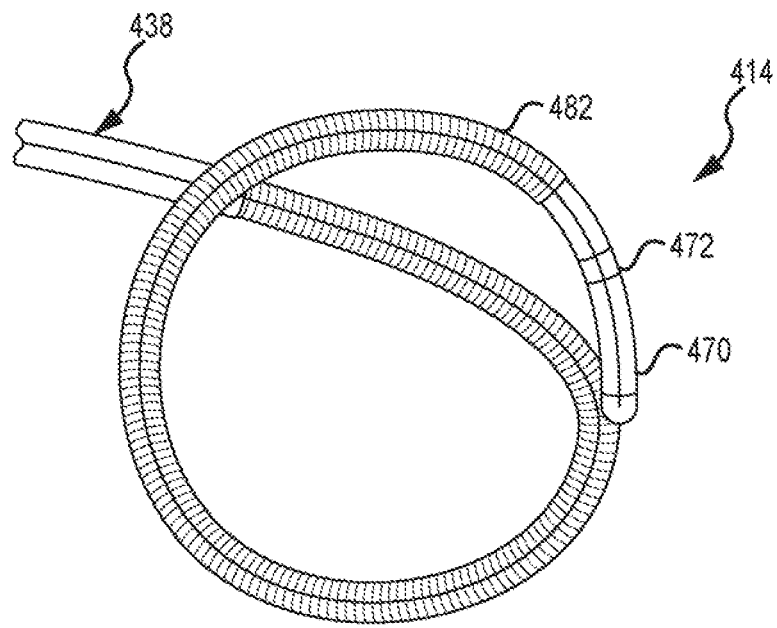

In FIG. 10a, the flexible sleeve 438 is shown as it can be and/or is moved into the fully extended position. In the fully extended position (also shown in FIG. 9a), the distal end 442 of the flexible sleeve 438 is at the distal end 436 of the guide element 432. During and exemplary procedure, the flexible sleeve 438 is moved to the fully extended position prior to contacting the tissue and beginning the procedure. Once positioned against the tissue in the desired location, the ablative element 444 can be and/or is activated, e.g., by delivering RF energy to the active region. Once a sufficient lesion has been formed in the fully extended position, the user can gradually retract the flexible sleeve 438, e.g., by operating the controller 438 to withdraw the flexible sleeve 438 generally in the direction of arrows 448a-c in FIG. 10a-c, respectively, so that the flexible sleeve 438 is in a partially retracted position (FIGS. 10b and 10c). The user can continue to retract the flexible sleeve 438 so that the flexible sleeve 438 continues to retract until the flexible sleeve 438 is in a fully retracted position, as illustrated in FIG. 10d.

Figure 10D:
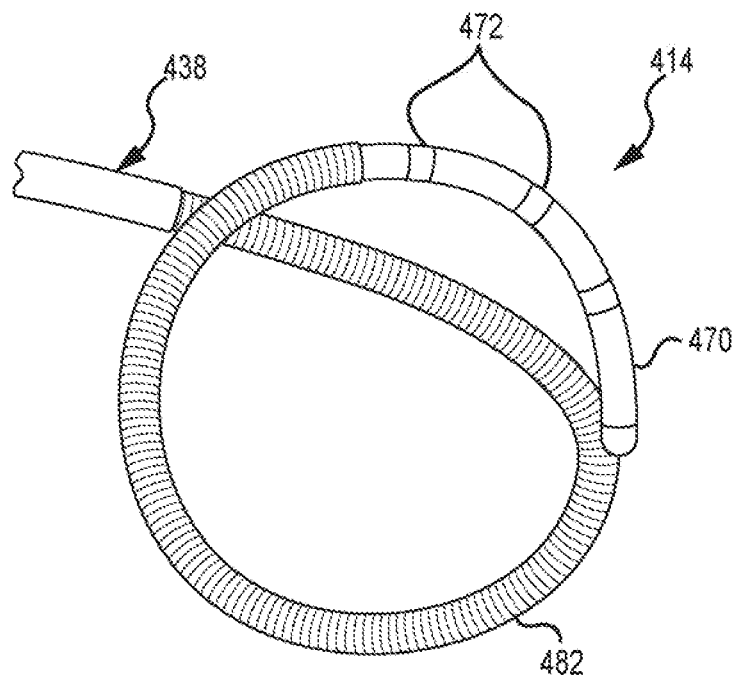
Figure 10E:
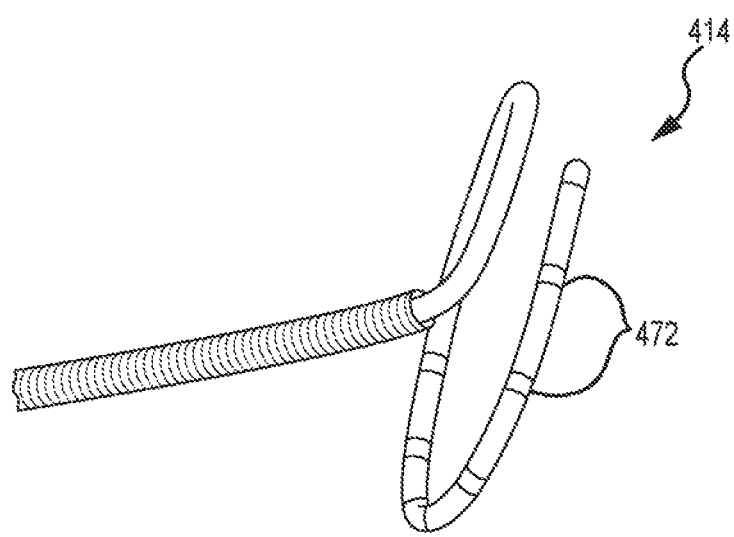

Again, the operation illustrated in FIG. 10a-d is not intended to illustrate discrete positions of the flexible sleeve 438, but rather to illustrate general movement from a fully extended position (as shown in FIG. 10a) to a fully retracted position (as shown in FIG. 10d). This motion can be and/or is a "fluid" or "smooth" motion (e.g., where the user moves the flexible sleeve 438 at a constant velocity); or the motion can be and/or is more segmented (e.g., where the user maintains the flexible sleeve 438 at one or more of these positions for a period of time before continuing moving the flexible sleeve 438). Specific operation will depend on the desired end-result, among other considerations for lesion formation.

Figure 11:
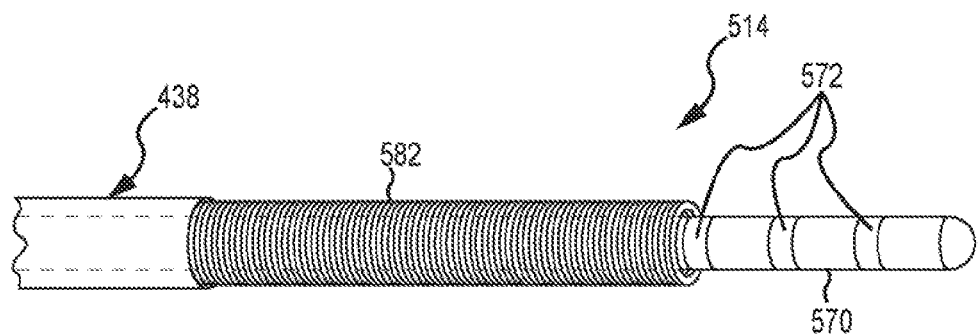
FIG. 11 shows another tip assembly having a generally linear configuration.
Figure 12:
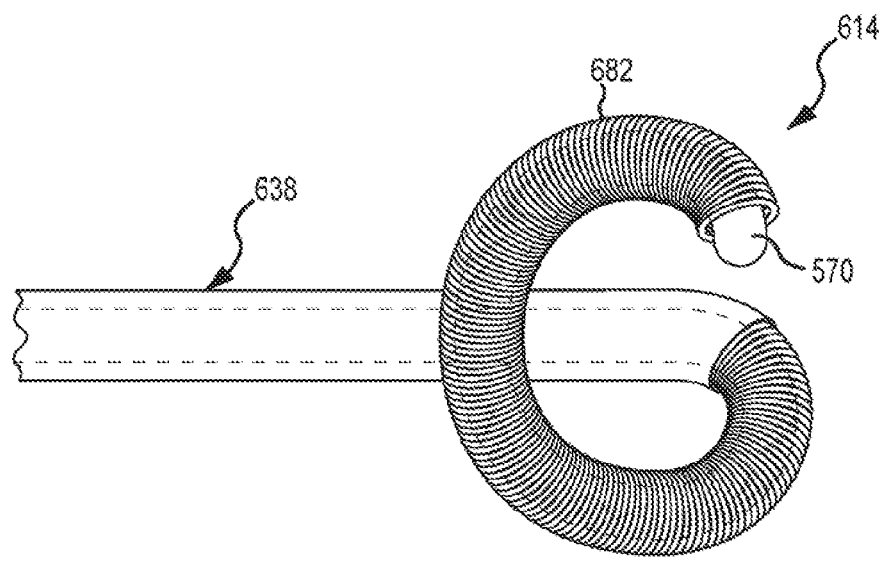
FIG. 12 shows another tip assembly having a generally flattened semi-circular configuration.
Figure 13A:
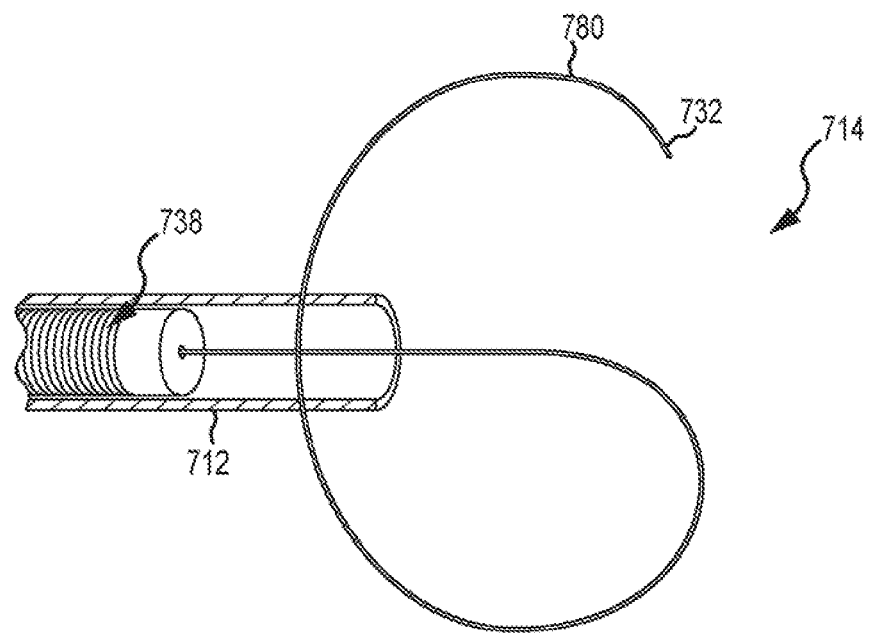
FIGS. 13a-b show another tip assembly having a guide wire guide element and a flexible sleeve, wherein (a) shows the flexible sleeve a fully extended position relative to the guide element; and (b) in a fully retracted position relative to the guide element.
Figure 13B:
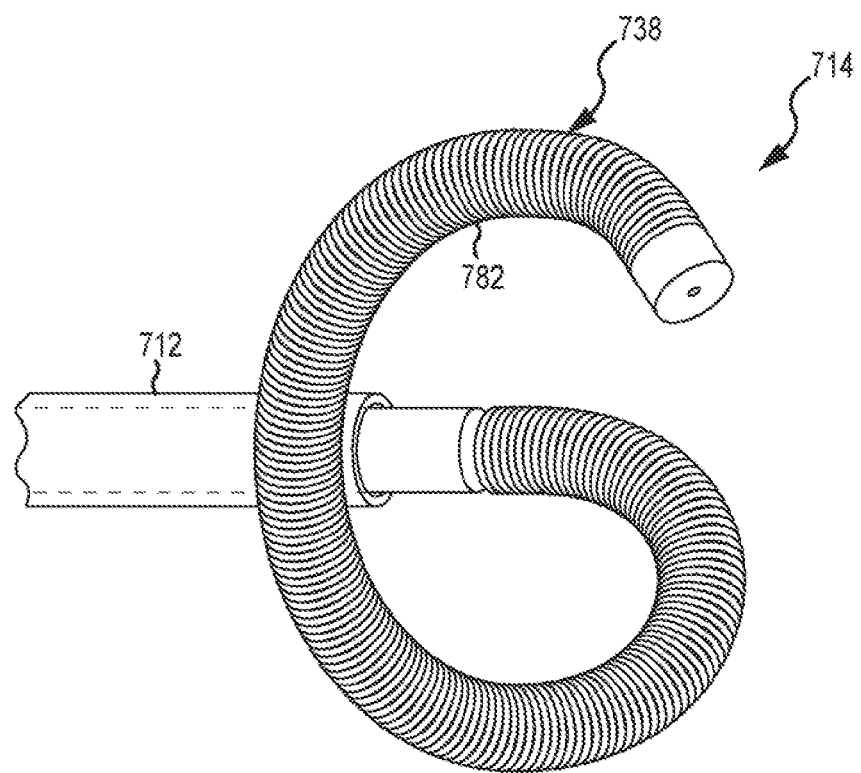

FIG. 11 shows another tip assembly 514 having a generally linear configuration, with catheter 570 having electrodes 572 and active portion 582. FIG. 12 shows another tip assembly 614 having a generally flattened semi-circular configuration and flexible sleeve 638 with active portion 682. FIGS. 13a-b show another tip assembly 714 having a guide wire 780 guide element 732 and a flexible sleeve 738. In FIGS. 13a and 13b, the flexible sleeve 738 is shown as it can be and/or is advanced through the catheter sheath 712 (see also, sheath 12 in FIG. 1 for reference). FIG. 13*a* shows the flexible sleeve 738 a fully extended position relative to the guide element 732. FIG. 13*b* shows the flexible sleeve 738 in a fully retracted position relative to the guide element 732. As already discussed above, the tip assemblies 514, 614, and 714 shown in FIGS. 11, 12, and 13*a*-b can be and/or is coupled through the sheath 712 (or tube portion 12 of the catheter 10 in FIG. 1) at one end, and provided through the sheath 712 for insertion into the patient's body.

The tip assemblies 514, 614, and 714 can include guide elements 532, 632, 732, respectively, which can be and/or is configurable in a desired shape. The tip assembly 614 can also include a flexible sleeve 538, 638, 738. The flexible sleeve 538, 638, 738 is made of a material which enables the flexible sleeve 538, 638, 738 to conform to the shape of the guide element 532, 632, 732 so that the flexible sleeve 538, 638, 738 can be slid over the guide element 532, 632, 732.

The tip assembly tip assemblies 514, 614, and 714 are particularly suited for ablation procedures wherein radio frequency waves are delivered at the site of an abnormal pathway in the body. Radiofrequency (RF) energy can therefore be coupled to biological tissue surrounding the catheter tip. Ablation procedures are typically used, for example, within the interior chambers of the heart to thermally ablate cardiac tissue. Accordingly, the flexible sleeves 538, 638, 738 can comprise an ablation element configured as the active portion, e.g., as already described above with reference with FIGS. 7 and 8.

A controller can be and/or is operatively associated with the tip assemblies 514, 614, and 714. The controller can be and/or is operated similarly to that already described above (e.g., including one or more pull wires), and therefore is not shown and described again with reference to the tip assemblies 514, 614, and 714.

While the invention has been described in terms of various specific embodiments, those skilled in the art will recognize that the invention can be practiced with modification within the spirit and scope of the claims.

What is claimed is:

1. A catheter comprising:
    a guide element including a proximal end and a distal most end, the distal end configurable in a circular shape extending at least 180 degrees and defining a circular path;
    a flexible sleeve conformable to the guide element so that the flexible sleeve slides over the guide element, the flexible sleeve including a proximal end and a distal end, the flexible sleeve including a conducting element, the conducting element of the flexible sleeve including both an insulating portion and an active portion of the conducting element;
    a controller attached to the flexible sleeve, the controller operable to move the flexible sleeve at least part way between the distal end of the guide element and the proximal end of the guide element;
    at least one ablation element formed by the active portion of the conducting element on the flexible sleeve at the distal end of the flexible sleeve, the at least one ablation element operable to form an ablative lesion when the flexible sleeve is adapted to be in contact with a contiguous volume of target tissue; and
    wherein the flexible sleeve is configured, during an ablation procedure, to be initially positioned at the distal most end of the guide element, and retracted toward the proximal end of the guide element during the ablation procedure, the retraction of the flexible sleeve along the circular path creates a lesion on the target tissue substantially conforming to the circular shape of the guide element.

2. The catheter of claim 1, wherein the guide element comprises one of a guide wire, a mapping catheter, and a preformed member configured into the circular shape.

3. The catheter of claim 1, wherein the conducting element is partially covered by the insulating portion, and the conducting element is electrically coupled to the active portion for delivering electrical energy to the active portion.

4. The catheter of claim 1, further comprising at least one electrode mounted to an outer surface of the flexible sleeve and at least one sensor mounted to an outer surface of the flexible portion.

5. The catheter of claim 4, wherein the at least one sensor comprises at least one of: a thermistor, a thermocouple, a mapping sensor, and a contact sensor.

6. The catheter of claim 1, wherein the circular shape of the guide element extends along a transaxial plane relative to a longitudinal axis of the catheter.

7. The catheter of claim 1, wherein the guide element includes an irrigation conduit with at least one irrigation port.

8. The catheter of claim 1, wherein the flexible sleeve forms both the insulating portion and the active portion of the conducting element.

9. The catheter of claim 1, wherein the insulating portion and the active portion are integral portions of the flexible sleeve.

10. The catheter of claim 1, wherein the flexible sleeve is coated over a portion of the conducting element to form the insulating portion.

11. A catheter comprising:
    a unitary flexible tubing including a proximal end and a distal end defining substantially an entire length of the catheter;
    a guide element including a proximal end and a distal most end, the distal end preformed in a circular shape extending at least 180 degrees and defining a circular path;
    a flexible sleeve conformable to the guide element so that the flexible sleeve slides over the guide element, the flexible sleeve including a proximal end and a distal end, the guide element and the flexible sleeve insertable through the unitary flexible tubing, the flexible sleeve including a conducting portion, the conducting portion of the flexible sleeve including both an insulating portion and an active portion;
    a controller attached to the flexible sleeve and extending through the unitary flexible tubing adapted for operation outside of a body of a patient, the controller operable to affect travel of the flexible sleeve over the guide element in two directions;
    at least one ablation element formed by an exposed portion of the active portion at the distal end of the flexible sleeve, the at least one ablation element operable to form an ablative lesion when the flexible sleeve is adapted to be in contact with a contiguous volume of target tissue; and
    wherein the travel of the flexible sleeve is constrained between an extended position toward the distal most end of the guide element and a retracted position toward the proximal end of the guide element, and the travel of the flexible sleeve is configured to create a lesion on the target tissue substantially conforming to the circular path of the guide element in contact with the target tissue by retracting the flexible sleeve during an ablation procedure from the extended position to the retracted position of the guide element.

12. The catheter of claim 11, wherein the guide element comprises one of a guide wire or a mapping catheter, and wherein the circular shape of the guide element extends along a transaxial plane relative to the length of the catheter.

13. The catheter of claim 11, wherein the active portion is in electrical contact with the conducting portion.

14. A catheter comprising:
a flexible tubing defining substantially an entire length of the catheter;
a guide including a proximal end and a distal most end, the distal end preformed in a circular shape that extends along a transaxial plane relative to the length of the catheter and defines a circular path;
a flexible sleeve conformable to the guide so that the flexible sleeve slides over the guide, the flexible sleeve including a proximal end and a distal end, the guide and flexible sleeve insertable through the flexible tubing for positioning adjacent a tissue, the flexible sleeve including a conducting portion, the conducting portion of the flexible sleeve including both an insulated portion and an active portion;
a control attached to the flexible sleeve and extending through the flexible tubing for operation outside of a patient's body to move the flexible sleeve back and forth over the guide means; and
an ablation element formed by an exposed portion of the active portion provided at the distal end of the flexible sleeve, the ablation element operable to form an ablative lesion when the flexible sleeve is adapted to be in contact with a contiguous volume of target tissue; and
wherein the flexible sleeve is configured to create a lesion on the contiguous volume of the target tissue substantially conforming to the circular path of the guide in contact with the target tissue by retracting the flexible sleeve during an ablation procedure from a distal most end to a proximal end of the guide.

15. The catheter of claim 14, wherein the guide is at least one of a guide wire or a mapping catheter, and the circular shape of the guide extends at least 180 degrees.

16. The catheter of claim 14, wherein moving the flexible sleeve creates a lesion on the tissue substantially conforming to the shape of the guide in contact with the tissue.

17. The catheter of claim 14, wherein the insulated portion surrounds part of the conducting portion; and the active portion is in electrical contact with the conducting portion.

18. The catheter of claim 14, further comprising at least one electrode mounted to an outer surface of the flexible sleeve.

* * * * *